United States Patent
Bacskai

(10) Patent No.: US 9,242,015 B2
(45) Date of Patent: Jan. 26, 2016

(54) DEVELOPMENT AND SCREENING OF CONTRAST AGENTS FOR IN VIVO IMAGING OF PARKINSON'S DISEASE

(75) Inventor: Brian Bacskai, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/882,997

(22) PCT Filed: Nov. 11, 2011

(86) PCT No.: PCT/US2011/060340
§ 371 (c)(1),
(2), (4) Date: Jun. 4, 2013

(87) PCT Pub. No.: WO2012/065045
PCT Pub. Date: May 18, 2012

(65) Prior Publication Data
US 2013/0259805 A1    Oct. 3, 2013

Related U.S. Application Data

(60) Provisional application No. 61/413,070, filed on Nov. 12, 2010.

(51) Int. Cl.
*A61K 49/00*   (2006.01)
*A61K 51/04*   (2006.01)
*G01N 33/68*   (2006.01)
*A61B 5/00*    (2006.01)

(52) U.S. Cl.
CPC ........... *A61K 49/0052* (2013.01); *A61K 49/003* (2013.01); *A61K 49/0028* (2013.01); *A61K 51/0453* (2013.01); *G01N 33/6896* (2013.01); *A61B 5/4082* (2013.01); *G01N 2800/2835* (2013.01)

(58) Field of Classification Search
CPC ....... A61K 31/12; A61K 31/27; A61K 49/00; A61K 51/04
USPC ................. 424/1.65, 1.85, 1.89, 9.1, 9.3, 9.6, 424/185.1, 186.2; 548/178, 217, 255, 468
See application file for complete search history.

(56) References Cited

U.S. PATENT DOCUMENTS 6,780,971 B2 *   8/2004   Wolozin et al. ............... 530/329
2009/0087376 A1 *   4/2009   Bacskai et al. ............... 424/1.65

OTHER PUBLICATIONS

Chang et al., J Med Chem, 52(11):3539-3547 (2009). "Structure-activity relationship of cyanine tau aggregation inhibitors."
Congdon et al., J Biol Chem, 284(31):20830-20839 (2009). "Inhibition of tau polymerization with a cyanine dye in two distinct model systems."
Honson et al., Biochem Biophys Res Commun, 363(1):229-234 (2007). "Potent inhibition of tau fibrillization with a multivalent ligand."
Masuda et al., Biochemistry, 45(19):6085-6094 (2006). "Small molecule inhibitors of alpha-synuclein filament assembly."

* cited by examiner

*Primary Examiner* — Michael G Hartley
*Assistant Examiner* — Jagadishwar Samala
(74) *Attorney, Agent, or Firm* — Nixon Peabody LLP

(57) ABSTRACT

The invention provides compounds and a method for imaging aggregated α-synuclein, e.g., Lewy bodies or Lewy neurites, in a tissue or organ.

20 Claims, 6 Drawing Sheets

DEVELOPMENT AND SCREENING OF CONTRAST AGENTS FOR IN VIVO IMAGING OF PARKINSON'S DISEASE

CROSS-REFERENCE TO RELATED APPLICATIONS

This application is a 35 U.S.C. §371 National Phase Entry Application of International Application No. PCT/US2011/060340 filed Nov. 11, 2011, which designates the U.S., and which claims the benefit under 35 U.S.C. §119(e) of U.S. Provisional Patent Application No. 61/413,070, filed Nov. 12, 2010, the contents of which are incorporated herein by reference in their entireties.

GOVERNMENT SUPPORT

This invention was made with government support under grant no. AG026240 awarded by the National Institutes of Health. The government has certain rights in the invention.

FIELD OF THE INVENTION

The invention relates to development and screening of contrast agents for in vivo imaging of Lewy bodies and Lewy neurites.

BACKGROUND OF THE INVENTION

Despite the discovery of Parkinson's disease (PD) in the early 1800s, a clinical diagnosis is still the prevailing method to assess the disease; there is no blood test or brain scan to diagnose PD. Post-mortem confirmation of the diagnosis is performed by the identification of Lewy bodies and Lewy neurites containing aggregated α-synuclein, the hallmark pathology of PD. Therefore, the existence of in vivo imaging technology for PD would greatly benefit patient diagnosis, disease treatments, and clinical research. In addition, an imaging contrast agent specific to PD pathology could be used to distinguish clinically similar neurodegenerative diseases such as Alzheimer's (AD), dementia with Lewy bodies (DLB), Parkinson's with dementia (PDD), and other Parkinsonian diseases.

The development of an in vivo imaging approach for Parkinson's disease patients would revolutionize clinical diagnosis and scientific research. Accordingly, there is need in the art for an agent that is specific for PD pathology to allow disease progression and drug efficacy to be imaged directly and non-invasively in vivo.

SUMMARY OF THE INVENTION

The invention is based in part on the surprising discovery by the inventors that fluorescent compounds with near infrared (NIR) spectra can be used to target and image aggregated α-synuclein, e.g., Lewy bodies or Lewy neurites. The inventors have discovered inter alia that certain NIR compounds, i.e. contrast agents, described herein preferentially bind to Lewy bodies or Lewy neurites. Accordingly, provided herein are methods for imaging aggregated α-synuclein, e.g., Lewy bodies or Lewy neurites, in a tissue or organ.

In one aspect, provided herein is a method for imaging of α-synuclein aggregation in a tissue or organ, the method comprising: contacting a compound described herein with a tissue or organ and detecting the compound bound to α-synuclein aggregate to image the aggregated α-synuclein. In some embodiments, of this and other aspects described herein the tissue or organ is brain of a subject.

The contacting can be in vitro, ex vivo, or in vivo. Accordingly, provided herein is a method for in vivo imaging of α-synuclein aggregates, the method comprising: administering a detectable amount of a contrast agent to a subject and detecting the contrast agent bound to the α-synuclein aggregate to image the α-synuclein aggregate in the subject.

In another aspect, provided herein is a method for detecting, diagnosing, or determining regression, progression, or onset of a Lewy body or Lewy neurite associated disorder, the method comprising: administering a detectable amount of a contrast agent to a subject in need thereof and detecting the contrast agent bound to α-synuclein aggregate to determine the amount or level of binding of the contrast agent to the α-synuclein aggregates. An increase in the amount or level of binding relative to a control level of binding indicates that the subject is suffering from or is at risk of developing a disorder associated with α-synuclein aggregation.

In yet in another aspect, provided herein is a method for evaluating a treatment for a Lewy body or Lewy neurite associated disorder, the method comprising: (a) administering a first detectable amount of a contrast agent to a subject undergoing treatment for a Lewy body or Lewy neurite associated disorder to obtain a first level of binding of the contrast agent to α-synuclein aggregate in the subject; (b) detecting the contrast agent bound to α-synuclein aggregate to determine the first level of binding of the contrast agent; (c) administering a second detectable amount of the contrast agent, wherein the second administration is at a time subsequent to the first administration, to obtain a second level of binding of the contrast agent to α-synuclein aggregate in the subject; (d) detecting the contrast agent bound to α-synuclein aggregate to determine the second level of binding of the compound; and (e) comparing the first level of binding with the second level of binding as an indication of the effectiveness of the treatment on the level of α-synuclein aggregate in the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows positive staining with high contrast (++). LDS-722 at 2 µM on a LB and LN. FIG. 2B shows positive staining with low contrast (+). NIAD-1 at 2 µM on a LB and LN. FIG. 2C shows negative staining (−). Oxazine 750 at 5 µM on a LB and LN. Post-mortem midbrain tissue from DLB and PD patients was obtained from the HBTRC Brain Bank at McLean Hospital. Tissue was fixed with formalin and immuno-stained with H3C primary antibody for synuclein and Alexa488 or Cy5 (not shown) conjugated secondary antibody. Immuno-stained tissue was incubated with fluorescent dyes in PBS at concentrations of 500 nM, 2 µM, and 5 µM for 30 minutes. Slides of tissue were imaged with Olympus Microscope at 60× with appropriate filter set. Examples of common staining patterns are illustrated to the left. Compounds showed variable binding affinities to Lewy bodies and neurites. Most dyes did not bind Lewy neurites. Many compounds were specific to Lewy bodies but had lower contrast and a few had higher contrast.

FIG. 3A shows staining with NIAD-1 and FIG. 3B shows staining with LDS-798. Paraffin-embedded formalin-fixed tissue from the temporal lobe of AD patients was obtained through the MA ADRC Brain Bank. Sections were stained with 0.05% Thio S to visualize plaques and NFT. Tissue was then stained with 5 µM dye in PBS. Slides were imaged on an Olympus Microscope at 20×, with a GFP emission filter for Thio S, and appropriate emission ranges for the dyes. Representative images are shown below. Many dyes had positive (+) staining for both plaques and tangles; however, some did not bind (−) AD pathology, suggesting a specificity for synuclein PD pathology.

FIG. 4A, Pittsburgh Compound B (PiB), a clinical PET ligand for amyloid imaging, was injected into the tail vein of a PD/APP transgenic mouse (18 mo) at a concentration of 10 mg/kg. The PiB compound was shown to cross the BBB within 1 minute of IV injection. Images were taken with a BIO-RAD MRC1024 multi-photon microscope. PiB fluorescence is seen within the vessel, crossing the vessel wall into the parenchyma, then binding amyloid pathology, and clearing the tissue rapidly. Bacskai B J, et al., PNAS, 2003, 100:12462-12467p. FIG. 4B, LDS798, which binds Lewy body pathology, was solubilized in 6% DMSO and 1×PBS at a concentration of 10 mg/kg and then injected IV into a wildtype mouse. Wide field fluorescence images were taken with a CCD camera on an Olympus microscope. The time course of fluorescence in the brain and vasculature during the bolus injection are shown.

DETAILED DESCRIPTION OF THE INVENTION

Figure 1:
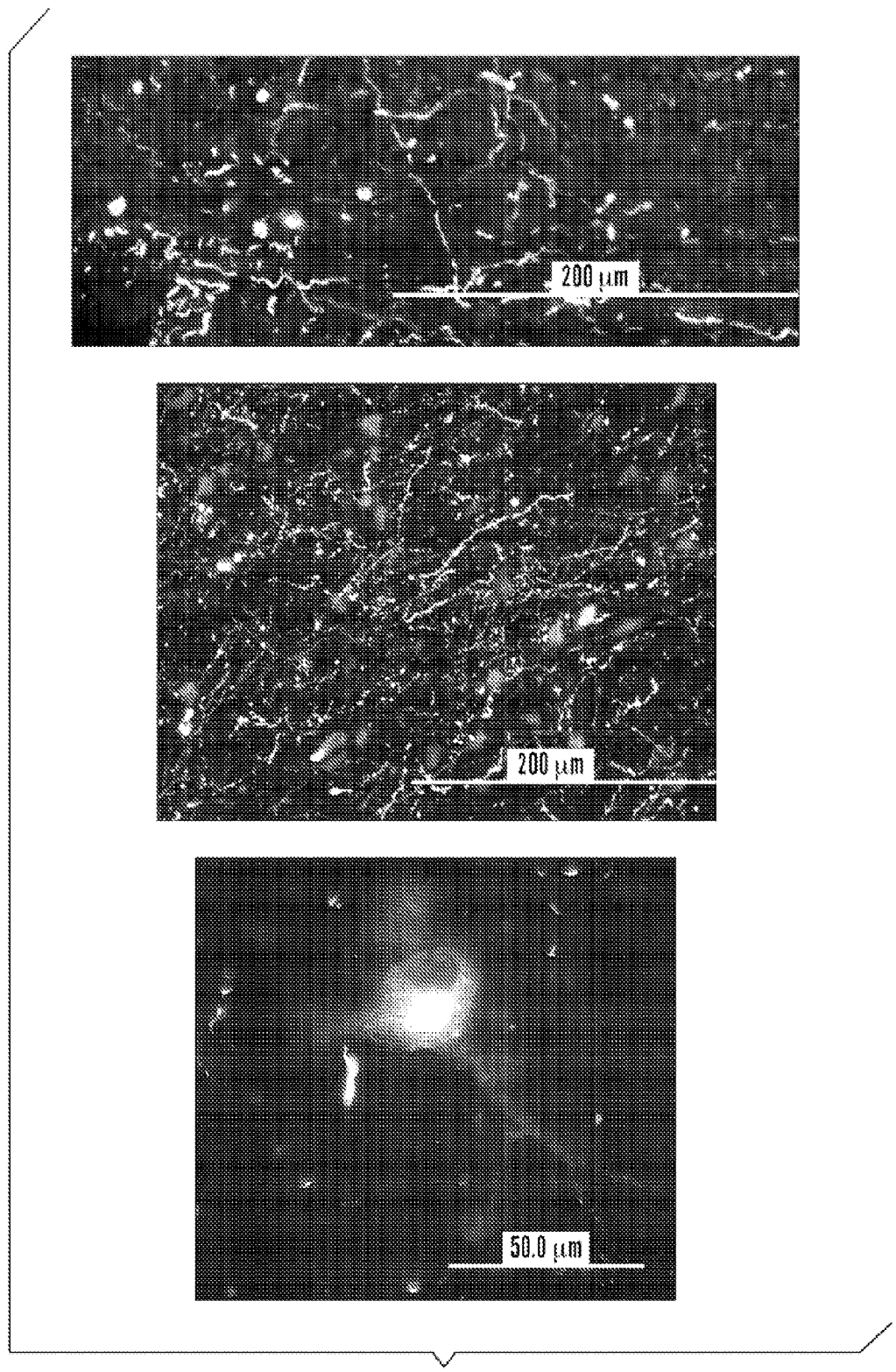
FIG. 1 is microscope images showing Lewy bodies and Lewy neurites are hallmarks of Parkinson's disease (PD) and Dementia with Lewy bodies (DLB) disease. PD/DLB tissue was stained with H3C antibody to synuclein and Alexa488-2° antibody. Imaged with Olympus Microscope using a GFP filter or with a white light broad filter to see synuclein and intracellular lipofuscin auto-fluorescence.

The inventors have discovered inter alfa that near infrared (NIR) fluorophores described herein preferentially bind with aggregated α-synuclein and thus can be used to target and image α-synuclein aggregates. Accordingly, in one aspect, provided herein is a method for imaging α-synuclein aggregation in a tissue or organ, the method comprising: contacting a contrast agent described herein with a tissue or organ and detecting the contrast agent bound to α-synuclein aggregate. Without wishing to be bound by a theory, detecting the contrast agent bound to α-synuclein aggregate can be used to determine the level of binding of the contrast agent, wherein the amount or level of binding indicates the amount of α-synuclein aggregation in the tissue.

The contacting of the contrast agent with the organ or tissue can be preformed in vitro, ex vivo, or in vivo. Accordingly, provided herein is also a method for in vivo imaging of α-synuclein aggregates in a subject, the method comprising: administering a detectable amount of a contrast agent to a subject and detecting the contrast agent bound to the α-synuclein aggregate to image the α-synuclein aggregate. The organ or tissue to be contacted can be a whole organ or tissue or part of an organ or tissue.

For in vitro or ex vivo contacting, the organ or tissue can be a biopsy or post-mortem tissue sample from a subject. Methods of obtaining biopsy or post-mortem tissue sample from a subject are well known in the art and readily available to an artisan. Additionally, for in vitro and ex vivo contact, the tissue or organ to be contacted can be in present in a buffer.

The methods of the invention, can include the determination of the presence, location and/or levels of α-synuclein aggregates in a tissue, organ or body area, preferably brain, spinal cord, or blood vessels of a subject. Thus, the methods and compositions described herein are also useful in the diagnosis of disorders associated with α-synuclein aggregation. Accordingly, in another aspect the invention provides a method for detecting, diagnosing, or determining regression, progression, or onset of a Lewy body or Lewy neurite associated disorder, the method comprising: administering a detectable amount of a contrast agent to a subject in need thereof and detecting the contrast agent bound to α-synuclein aggregate to determine the level of binding of the contrast agent. An increase in the level of binding relative to a control level of binding indicates that the subject is suffering from or is at risk of developing an α-synuclein aggregate associated disorder.

In some embodiments of the aspects described herein, detection of α-synuclein aggregate bound contrast agent is after a sufficient time has elapsed following administration for the contrast agent to bind with the α-synuclein aggregates. In some embodiments, detection is after 10 minutes, 15 minutes, 20 minutes, minutes, 25 minutes, 30 minutes, 45 minutes, 1 hour, 2 hours, 3 hours, 4 hours, 5 hours, 6 hours, 12 hours, 18 hours, 24 hours, 30 hours, 36 hours, 42 hours, 48 hours, or more time has elapsed following administration for the contrast agent to the subject.

Disorders associated with α-synuclein aggregation are disorders in which aggregation of α-synuclein is characteristic of the disorder. Exemplary disorders associated with α-synuclein aggregation include, but are not limited to, Parkinson's disease (PD), dementia with Lewy bodies and multiple system atrophy. Without limitations, the methods and compositions described herein can be used to diagnose Parkinson's disease, including the diagnosis of early-stage through advance-stage PD.

The methods described herein are also useful for longitudinal studies of α-synuclein aggregation in human populations at risk for α-synuclein aggregation, e.g. a subject suspected of having or at risk for having Lewy bodies or Lewy neurites. The methods of the invention permit the level of α-synuclein aggregation to be followed over time, allowing the determination of the correspondence between the timing α-synuclein aggregations relative to the onset of clinical symptoms. Thus, the methods described herein can be utilized to determine whether the level and timing of α-synuclein aggregation corresponds to α-synuclein aggregation associated disorder symptoms and severity. Additionally, the methods described herein can be used to determine the stage of an α-synuclein aggregation associated disorder in a subject.

The disclosed methods can also be used to monitor the effectiveness of treatments for α-synuclein aggregation associated disorders and/or treatment to reduce α-synuclein aggregation levels, or to stop an increase in α-synuclein aggregation levels. For example, a baseline level of α-synuclein aggregation can be obtained in a subject, a subsequent determination of the level of α-synuclein aggregation can be done, and the two levels compared. Such a comparison can provide information from the subject over time, allowing the assessment of efficacy of treatments provided to the subject. Thus, in one aspect, provided herein is a method for evaluating a treatment for an α-synuclein aggregation associated disorder, the method comprising: (a) administering a first detectable amount of a contrast agent to a subject undergoing treatment for an α-synuclein aggregation associated disorder to obtain a first level of binding of the contrast agent to α-synuclein aggregate in the subject; (b) detecting the contrast agent bound to α-synuclein aggregate to determine the first level of binding of the contrast agent; (c) administering a second detectable amount of the contrast agent, wherein the second administration is at a time subsequent to the first administration, to obtain a second level of binding of the contrast agent to α-synuclein aggregate in the subject; (d) detecting the contrast agent bound to α-synuclein aggregate to determine the second level of binding of the compound; and (e) comparing the first level of binding with the second level of binding as an indication of the effectiveness of the treatment on the level of α-synuclein aggregate in the subject.

As used herein, the phrase "evaluation of treatment" refers to the comparison of a subject's levels of α-synuclein aggregation measured at different measuring times, preferably at least one week apart, wherein the subject is undergoing treatment for an α-synuclein aggregation associated disorder. The first measurement can be before the onset of treatment regime. Alternatively, the first measurement can be after the treatment regime has already started.

In some embodiments, the second or subsequence level measurement from the subject is at least one week after obtaining the first measurement, which means the second measurement is obtained at any time following the week of the first measurement, preferably at least 1, 2, 3, 4, 5, 6, 7, 8, 9, 10, 15, 20, 25, 30, 35, 40, 45, 50, 55, 60, 65, 70, 80, 85, 90, 95, 100 or more weeks after the time of first level measurement in the subject.

The comparison of levels of α-synuclein aggregation, taken on different days, is a measure of the onset, progression, or regression of an α-synuclein aggregation associated disorder in a subject. Additionally, the comparison of two or more measurements of the level of α-synuclein aggregation in a subject allows evaluation of the treatment of the α-synuclein aggregation associated disorder that has been administered to the subject.

For example, an initial measurement of a subject's level of α-synuclein aggregation can indicate that the subject has an α-synuclein aggregation associated disorder and based on this assessment, treatment can be initiated in the subject. A subsequent measure of the level of α-synuclein aggregation from the subject can be used to determine the efficacy of the subject's treatment regime. Thus, a subsequent measure from a patient can allow the adjustment of therapy for an α-synuclein aggregation associated disease in the subject. The results of two or more determinations of a subject's α-synuclein aggregation levels can also be used in conjunction with behavioral measures, e.g. for dementia, and can provide information on the correlation between α-synuclein aggregation levels and dementia or other clinical manifestations of an α-synuclein aggregation associated disorder.

As will be appreciated by those of ordinary skill in the art, the evaluation of the treatment also can be based upon an evaluation of the symptoms or clinical end-points of the associated disease, such as the level of dementia and/or the progression of physical and/or mental functions that are characteristic of an α-synuclein aggregation associated disorder. Thus, the methods of the invention also provide for determining the regression, progression or onset of a condition which is characterized by abnormal levels of α-synuclein aggregation.

In some embodiments, the absence of change in the amount or level of α-synuclein aggregation in subsequent measurements from a subject can indicate that the progression of the α-synuclein aggregation associated disorder has halted or significantly slowed. The slowing or stopping of the progression of an α-synuclein aggregation associated disorder in a subject undergoing treatment for an α-synuclein aggregation associated disorder can be an indicator of the efficacy of the therapy and can be useful to determine and monitor the effective amount of a therapeutic compound for an α-synuclein aggregation associated disorder.

The methods of the invention include in part, measuring levels of α-synuclein aggregation, e.g., α-synuclein aggregates. Levels of α-synuclein aggregation can be determined in a number of ways when carrying out the various methods described herein. In some embodiments, the level of α-synuclein aggregation is measured by assessing a relative level of binding of contrast agent with the α-synuclein aggregates as described above. Such a relative measure can be expressed, for example, as a percentage of total detectable contrast agent used, e.g., introduced into the subject. For example, in gamma imaging, the relative measure can be expressed as a percentage of the total radiation administered to the subject. Another measurement of the level of α-synuclein aggregation is a measurement of absolute levels of α-synuclein aggregation. Another measurement of the level of α-synuclein aggregation is a measurement of the change in the level of -synuclein aggregation over time. This can be expressed in an absolute amount or can be expressed in terms of a percentage increase or decrease over time.

In some embodiments, levels of α-synuclein aggregation are advantageously compared to controls. The control can be a predetermined value, which can take a variety of forms. It can be a single cut-off value, such as a median or mean. It can be established based upon comparative groups, such as in groups without dementia or indication of risk for dementia and groups having dementia or having an indication of a risk or high risk of dementia. Another example of comparative groups would be groups having a particular disease (e.g. Parkinson's disease), condition or symptoms and groups without the disease, condition or symptoms. Another comparative group can be a group with a family history of a condition (e.g. Parkinson's disease) and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or amounts of α-synuclein aggregation and the highest quadrant or quintile being individuals with the highest risk or amounts of α-synuclein aggregation.

In some embodiments an internal control can be used to determine a relative amount α-synuclein aggregation. In some embodiments, the total level of the contrast agent in the tissue or region of interest in a test subject can be compared to the total level of the contrast agent in the same region of a control subject. In some instances, the control level can be the level previously obtained from the same region of the same test subject. In some embodiments of the invention, amount of contrast agent in the region of interest in a subject (region 1) can be determined along with the amount of contrast agent in another (control) region (region 2) of the subject's body. In some instances, for example in a subject suspected of having or at risk of having an α-synuclein aggregation associated disorder, the region of interest will be the cerebellum. The ratio of the level of contrast agent in region 1 to the contrast agent in region 2 can be compared to ratio of measurements taken from regions 1 and 2 of a normal control subject. Thus, in brain imaging, the amount (total or specific binding) of the bound contrast agent can be measured and compared (as a ratio) with the amount of contrast agent bound to the cerebellum of the subject. This ratio is then compared to the same ratio in age-matched normal brain, which serves as a control.

In some embodiments, the α-synuclein aggregation in a tissue or region or interest can be measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled contrast agent along with a large excess of unlabeled, but otherwise chemically identical contrast agent.

The predetermined value, of course, will depend upon the particular population selected. For example, an apparently healthy population will have a different 'normal' range than will a population which is known to have a condition related to abnormal α-synuclein aggregation. Accordingly, the predetermined value selected can take into account the category in which an individual falls. Appropriate ranges and categories can be selected with no more than routine experimentation by those of ordinary skill in the art. By abnormally high it is meant high relative to a selected control. Typically the control will be based on apparently healthy normal individuals in an appropriate age bracket. It will also be understood that the controls according to the methods described herein can be, in addition to predetermined values, samples of materials tested in parallel with the experimental materials. Examples include samples from control populations or control samples generated through manufacture to be tested in parallel with the experimental samples.

As mentioned above, it is also possible to characterize α-synuclein aggregation levels by monitoring changes in the absolute or relative amounts of α-synuclein aggregation over time. Without wishing to be bound by a theory, an increase in α-synuclein aggregation correlates with increasing severity of an α-synuclein aggregation associated disorder, e.g. correlates with the advancing stages of the disorder. Accordingly one can monitor α-synuclein aggregation levels over time to determine if α-synuclein aggregation levels of a subject are changing. An increase in the relative or absolute level of α-synuclein aggregation that is greater than 0.1% can indicate the onset or progression of an α-synuclein aggregation associated disorder. In some embodiments, the change in α-synuclein aggregation levels, which indicates onset or progression of an α-synuclein aggregation associated disorder, is 0.25% or greater, 0.5%, or greater, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, or 85% or greater.

Conversely, reductions in amounts of α-synuclein aggregation levels over time can indicate regression of an α-synuclein aggregation associated condition. Additionally, the absence of significant change in the amount of α-synuclein aggregation in a subject over time can mean the progression of an α-synuclein aggregation associated disorder has stopped or significantly slowed.

Methods described herein can be used to identify or measure α-synuclein aggregation in biopsy or post-mortem tissue. Thus, some embodiments of the invention include incubating formalin-fixed tissue with a solution of a contrast agent described herein. Preferably, the solution is 25-100% ethanol, (with the remainder being water) saturated with a contrast agent. Upon incubation, the contrast agent binds to and/or labels the α-synuclein aggregates in the tissue, allowing detection (e.g. visualization) of the α-synuclein aggregates by any standard method. Detection methods useful in this aspect of the invention can include microscopic techniques such as bright-field, fluorescence, laser-confocal and cross-polarization microscopy.

The method of quantifying the amount of α-synuclein aggregation in biopsy or post-mortem tissue involves incubating a contrast agent with homogenate of biopsy or post-mortem tissue. The tissue is obtained and homogenized by methods well known in the art. The contrast agent can include a radiolabel or fluorescent label or other detectable label such as enzymes, chemiluminescent molecules, etc, which are well known to skilled artisans. In some embodiments, the radiolabel is $^{125}$I, $^{14}$C or $^3$H which is contained in a substituent substituted on one of the compounds of the invention. Tissue containing α-synuclein aggregation will bind to the contrast agent and the bound tissue is then separated from the unbound tissue by any mechanism known to the skilled artisan, such as filtering. The bound tissue can then be quantified through any means known to the skilled artisan (e.g. scintillation counting, densitometry, etc). In some embodiments, the units of tissue-bound detectable label are converted to units of micrograms of α-synuclein aggregation per mg of tissue by comparison to a control. An example of a control useful in the methods of the invention is a standard curve generated by incubating known amounts of α-synuclein aggregates with the contrast agent.

The method of distinguishing an α-synuclein aggregation associated disorder brain from a normal brain involves obtaining tissue from (i) the cerebellum and (ii) another area of the same brain, other than the cerebellum, from normal subjects and from subjects suspected of having an α-synuclein aggregation associated disorder. Such tissues are made into separate homogenates using methods well known to the skilled artisan, and then are incubated with contrast agent. The amount of tissue which binds to the contrast agent is then calculated for each tissue type (e.g. cerebellum, non-cerebellum, normal, abnormal) and the ratio for the binding of non-cerebellum to cerebellum tissue is calculated for tissue from normal and for tissue from patients suspected of having a α-synuclein aggregation associated disorder. These ratios are then compared. For example, if the ratio from the brain suspected of having an α-synuclein aggregation associated disorder is 5% or above, 10% or above, 15% or above, 20% or above, 25% or above, 30% or above, 35% or above, 45% or above, 50% or above, 55% or above, 60% or above, 65% or above, 70% or above, 75% or above, 80% or above, 85% or above, or 90% or above of the ratios obtained from normal brains, the diagnosis of α-synuclein aggregation associated disorder is made. The normal ratios can be obtained from previously obtained data, or alternatively, can be recalculated at the same time the suspected brain tissue is studied. It will be understood that the percentage cut off for diagnosis of α-synuclein aggregation associated disorder can vary depending on the type of detectable label/reporter used. In some embodiments, a ratio that is diagnostic can be up to about 50%, 55%, 60%, 65%, 70%, 75%, 80%, 85%, 95% or more.

The methods described herein can also be used to determine the effectiveness of treatments for α-synuclein aggregation associated disorders and/or treatments to reduce α-synuclein aggregation levels, or to stop a increase in α-synuclein aggregation levels.

Contrast Agents

As used herein, the term "contrast agent" refers to a compound that binds an α-synuclein aggregate. A contrast agent can be a compound that preferentially binds α-synuclein aggregates compared to binding to a non α-synuclein amyloid protein.

Figure 5:
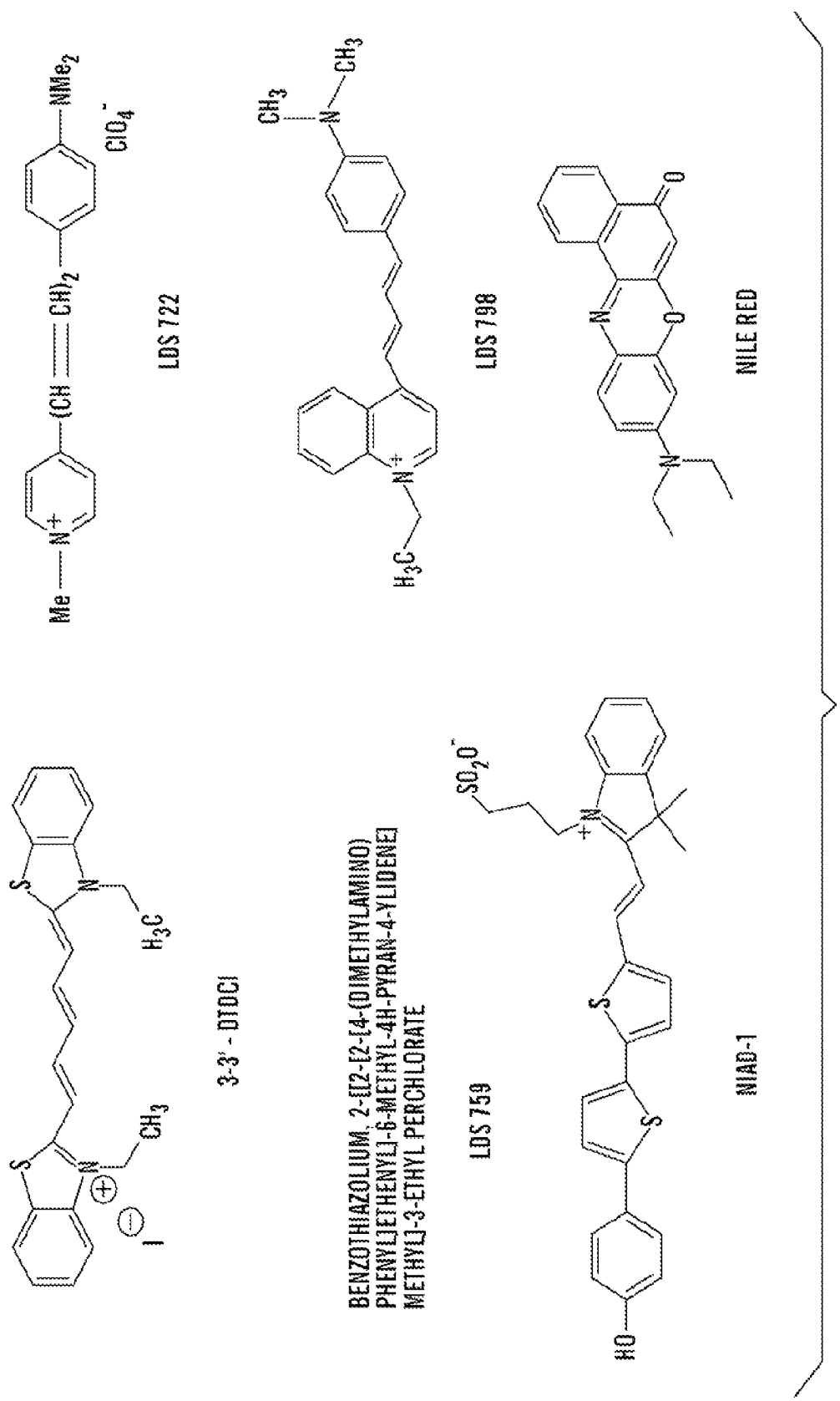
FIG. 5 shows the structures of some of the compounds described herein.
Figure 5:
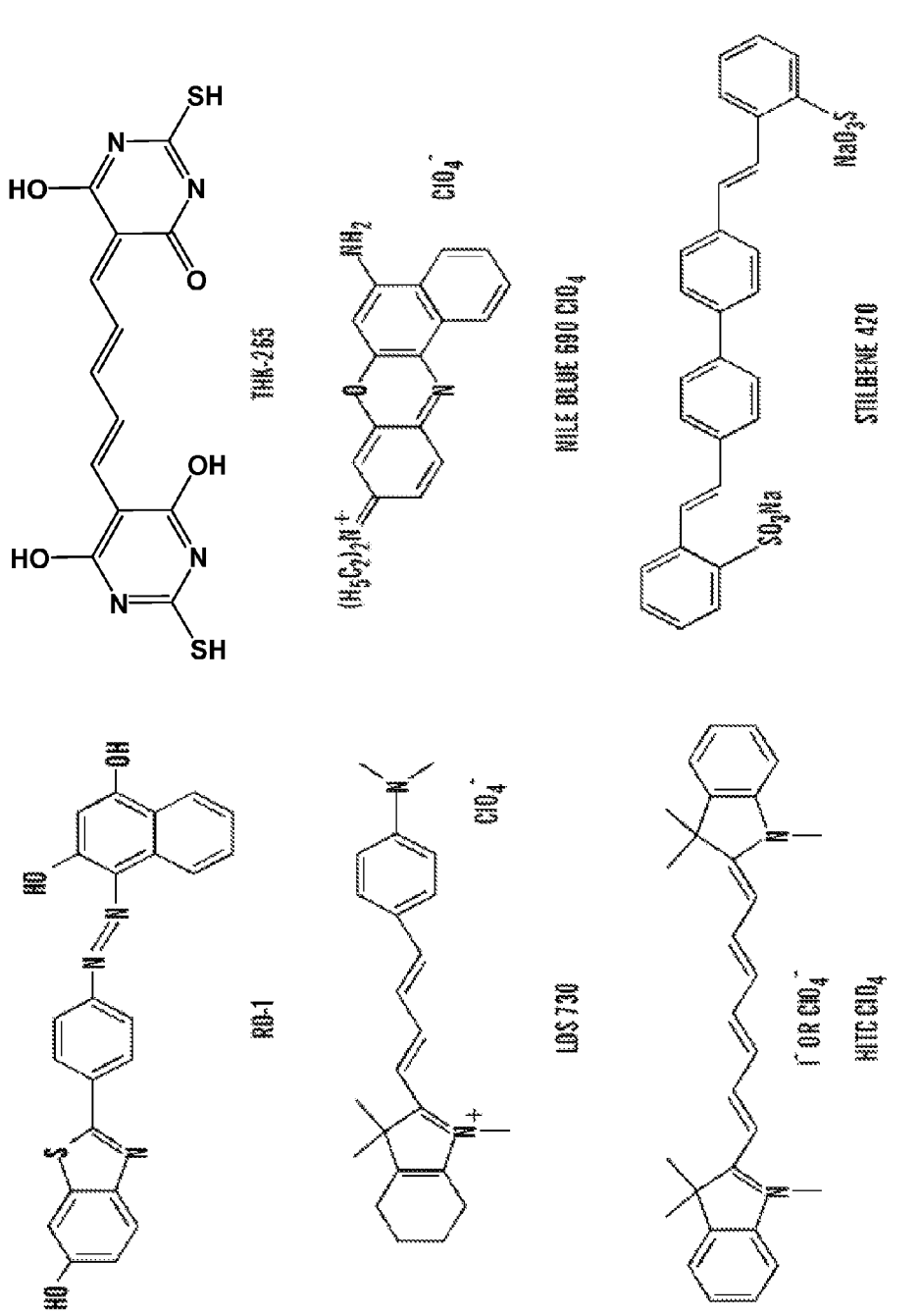

Exemplary contrast agents include but are not limited to 3,3'-diethylthiadicarbocyanine iodide (3-3'-DTDCI); 4-[4-[4-(dimethylamino)phenyl]-1,3-butadienyl]-1-ethyl-pyridinium perchlorate (LDS 722); LDS 759; 4-[4-[4-(dimethylamino)phenyl]-1,3-butadienyl]-1-ethyl quinolinium (LDS 798); NIAD-1; 9-diethylamino-5-benzo[α]phenoxazinone (Nile Red); RD-1; THK-265; 2-[4-[4-(dimethylamino)phenyl]-1,3-butadienyl]-1,3,3-trimethyl-3H-indolium perchlorate (LDS 730); 5-amino-9-(diethylamino)-benzo[a]phenoxazin-7-ium perchlorate (Nile Blue 690 $ClO_4$); 2-[7-(1,3-dihydro-1,3,3-trimethyl-2H-indol-2-ylidene)-1,3,5-heptatrienyl]-1,3,3-trimethyl-3H-indolium perchlorate (HITC $ClO_4$); 2,2"-([1,1'-biphenyl]-4.4'-diyldi-2,1-ethenediyl)bis-benzenesulfonic acid disodium salt (Stilbene 420); and pharmaceutically acceptable salts thereof. Structures of the exemplary contrast agents are shown in FIG. 5. Contrast agents also include analogs, derivatives, or isomers of the contrast agents described herein.

In some embodiments of the aspects described herein, the contrast agent is "labeled" with a radiolabel, fluorescent label, chemiluminescent label, or a combination thereof. Without wishing to be bound by a theory, labeling a contrast agent with a label allows detection of α-synuclein aggregate bound contrast agent by imaging techniques readily available to one of ordinary skill in the art. Choice of a label is dictated in part the imaging techniques to be employed. For example, radioactive isotopes and $^{19}F$ are particularly suitable for in vivo imaging in the methods of the present invention. Suitable radioisotopes for purposes of this invention include beta emitters, gamma-emitters, positron-emitters, and x-ray emitters. Thus, in some embodiments, the contrast agent is labeled with a beta-emitter, gamma-emitter, positron-emitter, x-ray emitter, or a combination thereof.

Suitable stable isotopes for use in Magnetic Resonance Imaging (MRI) or Magnetic Resonance Spectroscopy (MRS) include $^{19}F$ and $^{13}C$. Suitable radioisotopes for in vitro quantification of α-synuclein aggregates in homogenates of biopsy or post-mortem tissue include $^{125}I$, $^{14}C$, and $^{3}H$. Suitable radioisotopes for PET imaging include $^{11}C$ and $^{18}F$, and for SPECT imaging $^{123}I$. Accordingly, in some embodiments, the contrast agent is labeled with a radionuclide selected from the group consisting of $^{3}H$, $^{11}C$, $^{13}C$, $^{14}C$, $^{13}N$, $^{15}O$, $^{17}O$, $^{18}F$, $^{19}F$, $^{75}Br$, $^{76}Br$, $^{77}Br$, $^{82}Br$, $^{82}Rb$, $^{99m}Tc$, $^{123}I$, $^{124}I$, $^{125}I$, $^{131}I$, and any combinations thereof.

For purposes of in vivo imaging, the type of detection instrument available is a major factor in selecting a given label and will guide the selection of the radionuclide or stable isotope. For instance, the radionuclide chosen must have a type of decay detectable by a given type of instrument. Another consideration relates to the half-life of the radionuclide. The half-life should be long enough so that it is still detectable at the time of maximum uptake by the target, but short enough so that the host does not sustain deleterious radiation. The radiolabeled contrast agents can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range. For PET detection, the radiolabel will be a positron-emitting radionuclide such as 19F which will annihilate to form two 511 keV gamma rays which will be detected by the PET camera. Methods for multiphoton fluorescence excitation of a compound such as PIB include, but are not limited to, use of a 750-nm light from a mode-locked Ti:Sapphire laser, with fluorescence emission collected using a photomultiplier tube and an interference filter centered at 440 nm.

A contrast agent can be labeled any labeling method that does not completely abolish the binding of the contrast agent to an α-synuclein aggregate can be used. For instance, a contrast agent can be labeled by general organic chemistry techniques known to the art. See, for example, March, J. ADVANCED ORGANIC CHEMISTRY: REACTIONS, MECHANISMS, AND STRUCTURE (3rd Edition, 1985), content of which is incorporated herein by reference in its entirety. For example, a contrast agent can be radiolabeled with $^{18}F$, $^{11}C$, $^{75}Br$, or 76Br by techniques described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986), content of which is incorporated herein by reference in its entirety. A contrast agent can be radiolabeled with $^{123}I$ by any of several techniques known to the art. See, for example, Kulkami, Int. J. Rad. Appl. & Inst. (Part B) 18: 647 (1991), the contents of which are hereby incorporated by reference.

In addition, a contrast agent can be labeled with any suitable radioactive iodine isotope, such as, but not limited to $^{131}I$, $^{125}I$, or $^{123}$, by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio J. Org. Chem. 48: 4394 (1983); Goodman et al., J. Org. Chem. 49: 2322 (1984); Mathis et al., J. Labell. Comp. and Radiopharm. 1994: 905; Chumpradit et al., J. Med. Chem. 34: 877 (1991); Zhuang et al., J. Med. Chem. 37: 1406 (1994); and Chumpradit et al., J. Med. Chem. 37: 4245, (1994), content of all of which is incorporated herein by reference. For example, a stable triazene or tri-alkyl tin derivative of the compounds described herein is reacted with a halogenating agent containing $^{131}I$, $^{125}I$, $^{123}I$, $^{76}Br$, $^{75}Br$, $^{18}F$ or $^{19}F$.

A contrast agent can be radiolabeled with known metal radiolabels, such as Technetium-99m ($^{99m}Tc$). Modification of the substituents to introduce ligands that bind such metal ions can be effected without undue experimentation by one of ordinary skill in the radiolabeling art. Preparing radiolabeled derivatives of $^{99m}Tc$ is well known in the art. See, for example, Zhuang et al., Nuclear Medicine & Biology 26(2): 217-24, (1999); Oya et al., Nuclear Medicine & Biology 25(2): 135-40, (1998); and Horn et al., Nuclear Medicine & Biology 24(6):485-98, (1997), content of all of which is incorporated herein by reference.

In some embodiments, the contrast agent binds to an α-synuclein aggregate with a dissociation constant (KD) of between 0.0001 μM and 10 μM. The dissociation constant can be determined by measuring binding of the contrast agent to synthetic α-synuclein aggregate or a Parkinson's disorder brain tissue.

In some embodiments, the contrast agent can cross the blood brain barrier. Ability of a contrast agent to cross the blood brain barrier can be accessed by using an in vitro model of the blood brain barrier. In vitro models of blood brain barrier are described, for example in U.S. Pat. App. Pub. No.

2010/0233750; No. 2008/0044847; No. 2010/0273200; and No. 2010/0233750, and U.S. Pat. No. 5,260,210, content of all of which is incorporated herein by reference.

Detection Methods

For in vitro methods, α-synuclein bound contrast agent can be detected using methods well known in the art. For example, α-synuclein bound contrast agent can be detected using fluorescence assays, enzyme linked immunosorbent assays (ELISAs), immunoprecipitations, immunofluorescence, enzyme immunoassay (EIA), radioimmunoas say (RIA), Western blot analysis and other protocols well known in the art. Without wishing to be bound by a theory, in vitro detection methods include any method for detection or quantitation of ligand receptor binding, antibody antigen binding, and protein protein binding.

In vivo methods for detecting contrast agent bound to α-synuclein aggregates will necessarily vary depending upon factors specific to the subject and depending upon the body site under examination, method of administration and type of label used; the determination of specific procedures would be routine to the skilled artisan. For example with gamma imaging, the radiation emitted from the organ or area being examined can be measured and expressed either as total binding or as a ratio in which total binding in one tissue is normalized to (for example, divided by) the total binding in another tissue of the same subject during the same in vivo imaging procedure. However, any conventional method for detecting or visualizing diagnostic probes can be utilized in accordance with this invention.

For example, contrast agent bound to α-synuclein aggregate bound contrast agent can be imaged by routine imaging techniques such as infrared imaging, multiphoton imaging, gamma imaging, magnetic resonance imaging (MRI), magnetic resonance spectroscopy (MRS), near-infrared fluorescence (NIRF) imaging, position emission tomography (PET) imaging, single-photon emission computed tomography (SPECT or SPET) imaging, X-ray fluorescence imaging, PET with concurrent computed tomography (PET/CT), PET with concurrent magnetic CT imaging (SPECT/CT), planar scintillation imaging, any other appropriate imaging methods known to those of skill in the art, or a combination thereof.

Positron Emission Tomography (PET)

Positron Emission Tomography (PET) is a technique for measuring the concentrations and movement of positron-emitting radioisotopes within the tissues of living subjects. As is known in the art, PET is a type of nuclear medicine imaging in which very small amounts of radioactive materials are used to diagnose diseases. A radioactive tracer, e.g., a radiolabeled contrast agent is injected into a vein, swallowed by mouth or inhaled as a gas and eventually collects in the area of a human body being examined, where it gives off energy in the form of gamma rays. This energy is detected by a PET scanner and the distribution of the positron activity as a function of time is then imaged as a function of time by means of emission tomography. These devices work together with a computer to measure the amount of radio active tracer absorbed by a body and to produce special pictures offering details on both the structure and function of organs and other internal body parts.

PET imaging is indirect and relies on computerized reconstruction procedures to produce tomographic images. PET imaging uses tomography to detect positron-emission. Radionuclide decay reduces excess positive charges on the nucleus in two ways: (1) neutralization of a positive charge with the negative charge of an electron or (2) the emission of a positron from the nucleus. The positron then combines with an electron from the surrounding environment and annihilates. Upon annihilation, both the positron and the electron are then converted to electromagnetic radiation, in the form of two high-energy (511-keV) gamma rays (photons), which are emitted 180 degrees away from each other. The resulting radiation can be detected externally using crystal scintillation detectors and is used to measure the quantity and the location of the positron-emitting source. Simultaneous detection of these two photons by detection means placed on opposite sides of an object (e.g. the patient's eyes or the patient's head) establishes the site of positron annihilation on or about a line connecting the centers of the two detection means. The crystal scintillation detectors detect the emitted photons and tomographically reconstruct the point of origin of the positron-electron collision. Burggren et al., Curr Topics in Med. Chem. 2:385-93 (2002), incorporated herein by reference.

The PET technique depends on simultaneous or coincident detection of the pair of photos and consequently, photons which do not arrive in pairs are ignored. PET scans are increasingly read alongside CT or MRI scans since the combination gives both anatomic and metabolic information. Because the two scans can be performed in immediate sequence during the same session and the subject or patient does not have to change position, the two sets of images are more-precisely registered so that areas of abnormality on the PET imaging can be more perfectly correlated with anatomy on the CT images.

Generally, positron-emitting radionuclides have short half-lives and high radiation energies, when compared with radioisotopes generally used in biomedical research. Examples of positron-emitting radionuclides used in PET include: Carbon-11, Nitrogen-13, Oxygen-15, and Fluorine-18, which have half-lives of 20 minutes, 10 minutes, 2 minutes, and 110 minutes, respectively. These radioactive forms of the natural elements that emit radiation that will pass through the body for external detection. An advantage of this method of detection is that the short half-lives of the radionuclides used allow large doses to be administered to patients with low radiation exposure, which, in turn, enables studies to be repeatedly performed.

Single Photon Emission Computed Tomography (SPECT)

Single photon emission computed tomography (SPECT or SPET) is a nuclear medicine tomographic imaging technique that uses gamma rays. The system shares a number of similarities with conventional nuclear medicine planar imaging using a gamma camera; however, SPECT is capable of providing true 3D information. This information is typically presented as cross-sectional slices through the patient or animal; however, the information can be presented in other ways and can be freely reformatted or manipulated as required. SPECT imaging is performed using a gamma camera to acquire multiple 2D images (projections) from multiple angles. A computer is then used to apply a tomographic reconstruction algorithm to the multiple projections to yield a 3D dataset. This dataset can be manipulated to show thin slices along any chosen axis of the body similar to those obtained using other imaging techniques, such as MRI, CT and PET.

To acquire SPECT images, the gamma camera is rotated around the patient and projections (images) are acquired at defined points during the rotation, typically every 3-6 degrees. Conventionally, a full 360 degree rotation is used to obtain an optimal reconstruction. Multi-headed gamma cameras can be used to accelerate the acquisition process. SPECT can be used to complement any gamma imaging study where a true 3D representation can be helpful.

Magnetic Resonance Imaging (MRI)

Magnetic resonance imaging (MRI) is an imaging technique used in medical settings to produce high quality images of the inside of the human body. In MRI imaging, radio waves generated in a strong magnetic field are used to provide information about hydrogen atoms in different tissues within a human body. A computer uses this information to produce two and three dimensional images of the tissues in many different planes. For example, human tissues that are well-visualized using MRIs include soft tissues such as the brain and spinal cord, abdomen, and joints. Structural MRI provides a tool useful for observing structural differences in a non-invasive manner. Burggren et al., Curr Topics in Med. Chem. 2:385-93 (2002), incorporated herein by reference. After placing a subject into a strong magnetic field, the application of a brief radio frequency electromagnetic pulse disturbs the equilibrium of the proton nuclei within a subject and introduces a magnetization that can be detected as a radio signal and formed into an image.

MRI uses radio waves and a strong magnetic field rather than x-rays to provide clear and detailed pictures of internal organs and tissues such as brain and ocular tissues. The technique is used to evaluate some body structures e.g. brain that may be difficult to image visible with other imaging methods. For example, MRI can be used to produce a high resolution image of the brain's internal structure.

After placing a subject into the strong magnetic field, the application of a brief radio frequency electromagnetic pulse disturbs the equilibrium of the proton nuclei within a subject and introduces a magnetization that can be detected as a radio signal and formed into an image. Because the rate at which a magnetic resonance (MR) signal decays in these protons depends on intrinsic factors, signals decay at different rates in different tissue types. Thus, the resulting image contains different signal intensities in various regions of the body depending on the decay rate to the protons that make up that area.

An MRI scanner contains a large magnet that induces different chemical elements to emit distinctive radio signals. This signal data is then translated into 2-D pictures of the brain, slice by slice, and the resulting 2-D pictures can be combined to create 3-D views.

MRI equipment includes a horizontal tube (the bore of the magnet) running through the magnet from front to back. The magnetic force exerted on an object increases exponentially as it nears the magnet. The MRI machinery applies a radio frequency (RF) pulse that is specific only to hydrogen. The system directs the pulse toward the area of the body being examined. This pulse then causes the protons in the area under examination to absorb the energy required to make them spin ("precess") in a different direction, which is known as the "resonance" part of MRI. The RF pulse forces the one or two extra, unmatched protons per million to spin at a particular frequency and in a particular direction. This frequency is known as the Larmour frequency, which can be calculated, based on the particular tissue being imaged and the strength of the main magnetic field of the MRI equipment.

Typically, RF pulses are applied through coils that conform to the part of the body being examined and that are located within the MRI machinery. Almost simultaneously, the three gradient magnets are activated, which are arranged in such a manner inside the main magnet that when they are turned on and off very rapidly in a specific manner, they alter the main magnetic field on a very local level.

When the RF pulse is turned off, the hydrogen protons begin to slowly return to their natural alignment within the magnetic field and release their excess stored energy, thereby giving off a signal that is picked up by the coil and sent to the computer system. This mathematical data is converted, through the use of a Fourier transform, into a picture that can be put on film. This step represents the "imaging" part of MRI. Imaging modalities such as MRI use injectable contrasts, or dyes, for certain procedures. MRI contrast works by altering the local magnetic field in the tissue to be examined. Normal and abnormal tissue will respond differently to this slight alteration, which yields differing signals that are transferred to the images, allowing us to visualize many different types of tissue abnormalities and disease processes.

Functional Magnetic Resonance Imaging (fMRI)

fMRI is a technique that has several advantages over PET, such as noninvasiveness, increased spatial and temporal resolution, and repeatability because fMRI does not involve exposure to radiation. For example, fMRI monitors blood flow, which is a marker for neural activity, during an active state to assess which regions are involved in the completion of the task. When used to detect Parkinson's Disease, a "cognitive stress test" can be used to identify subtle abnormalities that would normally go undetected in a resting state. In some embodiments, fMRI and PET are used in conjunction to improve the early detection of an α-synuclein aggregation associated disorder.

When particular neural regions become more active, a corresponding change in glucose and oxygen utilization is observed. As oxygenated and deoxygenated hemoglobin have slightly different magnetization properties fMRI defects changes in blood supply when brain regions are activated during a particular task. Pauling et al., Proc. Natl. Acad. Sci. USA 22:210-216 (1936). MR signals, which are induced by an RF pulse, decay more rapidly for deoxyhemoglobin than for oxyhemoglobin, and this contrast ("blood oxygenation level-dependent (BOLD) contrast") is visualized and formed into an image. Ogawa et al., Proc. Natl. Acad. Sci USA 87:9868-72 (1990). The increase in oxygenated blood levels following neural activity appears to greater than what is actually used by an active region. Fox et al., Proc. Natl. Acad. Sci USA 83:1140-44 (1986). Therefore, a comparison of the excess of oxygenated blood on the venous side compared to the resting state can be used to determine which neural regions are active during a particular task. Burggren et al., Curr Topics in Med. Chem. 2:385-93 (2002), incorporated herein by reference.

Near-Infrared Fluorescence (NIRF) Imaging

Near-infrared fluorescence (NIRF) imaging is a non-invasive, non-isotopic method for optical imaging technique for method for in vivo imaging using a fluorophore. Of the various optical imaging techniques, near-infrared fluorescence (NIRF) imaging is of particular interest for non-invasive in vivo imaging because of the relatively low tissue absorbance, minimal autofluorescence of near-infrared (NIR) light, and deep tissue penetration of up to 6-8 centimeters.

In near-infrared fluorescence imaging, a laser or appropriately filtered light with a defined bandwidth is used as a source of fluorescence excitation. The excitation light travels through body tissues. When it encounters a near-infrared fluorescent molecule, e.g., a contrast agent, or a contrast agent labeled with a NIR fluorophore, the excitation light is absorbed. The NIRF then emits light as fluorescence with a longer wavelength and therefore spectrally distinguishable from the excitation light. For NIRF imaging, a contrast agent typically fluoresces in the near-infrared (NIR) region (in the range of 600-1100 nm), e.g., after excitation in the far-red range of visible light wavelengths.

Fluorescence imaging can be carried out using any suitable imaging camera or device. A number of reflectance and tomographic imaging systems have been developed to detect NIR fluorescence in deep tissues. In some embodiments, the fluorescence image is NIRF imaging, e.g., by fluorescence mediated tomography (FMT) or surface reflectance imaging.

Besides being non-invasive, NIR fluorescence imaging methods offer a number of advantages over other imaging methods: they provide generally high sensitivity, do not require exposure of test subjects or lab personnel to ionizing radiation (as can be required by the use of radioactively-labeled proteins), offer the possibility of repeated and frequent use of the imaging procedure, can allow for simultaneous use of multiple, distinguishable contrast agents and offer high temporal and spatial resolution (important in functional imaging and in vivo microscopy, respectively).

Computed Tomography (CT)

Yet another imaging technique is computed tomography (CT) which is an imaging method employing tomography. Digital geometry processing is used to generate a three-dimensional image of the inside of an object from a large series of two-dimensional X-ray images taken around a single-axis of rotation. CT produces a volume of data which can be manipulated through a process that is known as windowing.

Pharmaceutical Compositions

For administration to a subject, the contrast agent can be provided in pharmaceutically acceptable compositions. These pharmaceutically acceptable compositions comprise a contrast agent, formulated together with one or more pharmaceutically acceptable carriers (additives) and/or diluents. The pharmaceutical composition can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the contrast agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

The amount of a contrast agent that can be combined with a carrier material to produce a single dosage form will generally be that amount of the contrast agent that is produces a detectable amount after administration to the subject. Generally out of one hundred percent, the amount of the contrast agent will range from about 0.01% to 99%, preferably from about 1% to about 80%, more preferably from about 5% to about 70%, and most preferably from 10% to about 30%.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "detectable amount" as used herein means that amount of a contrast agent which is sufficient to enable detection of the contrast agent bound to α-synuclein aggregate. A detectable amount includes that amount of a contrast agent that is sufficient to enable imaging of binding of the contrast agent bound to α-synuclein aggregate. Determination of a detectable amount is well within the capability of those skilled in the art. Generally, a detectable amount can vary with the subject's history, age, condition, sex, as well as the severity and type of the medical condition in the subject, mode of administration, administration of other compounds or compositions, and particular imaging method employed.

The detectable amount can be estimated initially from in vivo assays. A dose may be formulated in animal models to achieve a circulating plasma concentration range that includes the concentration of the contrast agent which achieves a optimal signal-to-noise ratio as determined in in vivo assay. Levels in plasma can be measured, for example, by high performance liquid chromatography.

Generally, the compositions are administered so that a contrast agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

A contrast agent can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Administration to the subject can be local or systemic and accomplished intravenously, intraarterially, intrathecally (via the spinal fluid) or the like. Administration can also be intradermal or intracavitary, depending upon the body site under examination. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the aspects described herein, the contrast agent is administered by intravenous infusion or injection.

Subject

As used herein, a "subject" means a human or animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., *Rhesus*. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of conditions or disorders associated with Lewy body or Lewy neurite associated disorders. In addition, the methods and compositions described herein can be used to treat domesticated animals and/or pets.

A subject can be one who is suspected of having or predisposed to developing a disorder characterized by α-synuclein aggregation.

A subject can be one who is suspected of having or predisposed to Parkinson' disease.

A subject can be one who has been previously diagnosed with or identified as suffering from or having a disorder characterized by α-synuclein aggregation (e.g., Lewy bodies or Lewy neurites).

A subject can be one who has been previously diagnosed with or identified as suffering from or having Parkinson' disease.

A subject can be one who is currently undergoing a treatment for a disorder characterized by α-synuclein aggregation (e.g., Lewy bodies or Lewy neurites).

A subject can be one who is currently undergoing a treatment for Parkinson' disease.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

By "treatment", "prevention" or "amelioration" of a condition, disease and/or disorder associated with α-synuclein aggregation is meant delaying or preventing the onset, reversing, alleviating, ameliorating, inhibiting, slowing down or stopping the progression, aggravation or deterioration the progression or severity of a condition, disease and/or disorder characterized or associated with α-synuclein aggregation. In some embodiments, at least one symptom associated with a condition, disease and/or disorder characterized or associated with α-synuclein aggregation is alleviated by at least 5%, at least 10%, at least 20%, at least 30%, at least 40%, or at least 50% relative to before onset of treatment.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The invention can be described by one or more of the following numbered paragraphs:

1. A method for in vivo imaging of an α-synuclein aggregate, the method comprising:
    a) administering, to a subject in need thereof, a detectable amount of a compound selected from the group consisting of 3,3'-diethylthiadicarbocyanine iodide (3-3'-DTDCI); 4-[4-[4-(dimethylamino)phenyl]-1,3-butadienyl]-1-ethyl-pyridinium perchlorate (LDS 722); LDS 759; 4-[4-[4-(dimethylamino)phenyl]-1,3-butadienyl]-1-ethyl quinolinium (LDS 798); NIAD-1; 9-diethylamino-5-benzo[α]phenoxazinone (Nile Red); RD-1; THK-265; 2-[4-[4-(dimethylamino)phenyl]-1,3-butadienyl]-1,3,3-trimethyl-3H-indolium perchlorate (LDS 730); 5-amino-9-(diethylamino)-benzo[a]phenoxazin-7-ium perchlorate (Nile Blue 690 $ClO_4$); 2-[7-(1,3-dihydro-1,3,3-trimethyl-2H-indol-2-ylidene)-1,3,5-heptatrienyl]-1,3,3-trimethyl-3H-indolium perchlorate (HITC $ClO_4$); 2,2"-([1,1'-biphenyl]-4.4'-diyldi-2,1-ethenediyl)bis-benzenesulfonic acid disodium salt (Stilbene 420); analogs, derivatives, isomers and pharmaceutically acceptable salts thereof; and any combinations thereof; and
  b) detecting the contrast agent bound to the α-synuclein aggregate to image the α-synuclein aggregate.
2. The method of paragraph 1, wherein the subject is suspected of having a Lewy body or Lewy neurite associated disorder.
3. A method for detecting, diagnosing, or determining regression, progression, or onset of a Lewy body or Lewy neurite associated disorder, the method comprising:
  a) administering, to a subject in need thereof, a detectable amount of a compound selected from the group consisting of 3-3'-DTDCI, LDS 722, LDS 759, LDS 798, NIAD-1, Nile Red, RD-1, THK-265, LDS 730, Nile Blue 690 $ClO_4$, HITC $ClO_4$, Stilbene 420, and any combinations thereof; and
  b) detecting the compound bound to α-synuclein aggregate to determine the level of binding of the contrast agent, wherein an increase in the level of binding relative to a control level of binding indicates that the subject is suffering from or is at risk of developing an α-synuclein aggregate associated disorder.
4. A method of evaluating a treatment for a Lewy body or Lewy neurite associated disorder, the method comprising:
  a) administering a first detectable amount of a compound to a subject undergoing treatment for a Lewy body or Lewy neurite associated disorder to obtain a first level of binding of the compound to α-synuclein aggregate in the subject;
  b) detecting the compound bound to α-synuclein aggregate to determine the first level of binding of the compound;
  c) administering a second detectable amount of the compound, wherein the second administration is at a time subsequent to the first administration, to obtain a second level of binding of the compound to α-synuclein aggregate in the subject;
  d) detecting the compound bound to α-synuclein aggregate to determine the second level of binding of the compound; and
  e) comparing the first level of binding with the second level of binding as an indication of the effectiveness of the treatment on the level of α-synuclein aggregate in the subject,
    wherein the compound is selected from the group consisting of 3-3'-DTDCI, LDS 722, LDS 759, LDS 798, NIAD-1, Nile Red, RD-1, THK-265, LDS 730, Nile Blue 690 $ClO_4$, HITC $ClO_4$, Stilbene 420, and any combinations.
5. The method of any of paragraphs 2-4, wherein the Lewy body or Lewy neurite associated disorder is Parkinson's disease.
6. The method of any of paragraphs 1-5, wherein the α-synuclein aggregate is located in the brain of the subject.
7. The method of any of paragraphs 1-6, wherein the detectable amount of the compound is from about 1 µg/kg body weight to about 250 mg/kg body weight.
8. The method of any of paragraphs 1-7, wherein said administering is by intravenous injection.
9. The method of any of paragraphs 1-8, wherein the subject is human.
10. A method of detecting α-synuclein aggregates in a tissue, the method comprising:
  a) contacting a compound with a tissue, wherein the contrast agent is selected from the group consisting of 3-3'-DTDC1, LDS 722, LDS 759, LDS 798, NIAD-1, Nile Red, RD-1, THK-265, LDS 730, Nile Blue 690 $ClO_4$ HITC $ClO_4$, Stilbene 420, and any combinations thereof; and
  b) detecting the compound bound to α-synuclein aggregate to determine the level of binding of the compound, wherein the level of biding indicates the amount of α-synuclein aggregate in the tissue.
11. The method of paragraph 10, wherein the tissue is a brain tissue.
12. The method of any of paragraphs 10-11, wherein said contacting is in vitro.
13. The method of any of paragraphs 10-11, wherein said contacting is in vivo.
14. The method of paragraph 13, wherein said contacting is in a mammal.
15. The method of any of paragraphs 1-14, wherein said detecting is by infrared imaging, multiphoton imaging, gamma imaging, magnetic resonance imaging (MRI), magnetic resonance spectroscopy, or a combination thereof.
16. The method of any of paragraphs 1-15, wherein said detecting is by near-infrared fluorescence (NIRF) imaging, position emission tomography (PET) imaging, single-photon emission computed tomography (SPECT or SPET) imaging, X-ray fluorescence imaging, PET with concurrent computed tomography (PET/CT), PET with concurrent magnetic CT imaging (SPECT/CT), or a combination thereof.
17. The method of any of paragraphs 1-16, wherein the compound is labeled with a radiolabel, fluorescent label, chemiluminescent label, or a combination thereof.
18. The method of any of paragraphs 1-17, wherein the compound is labeled with a beta-emitter, gamma-emitter, positron-emitter, x-ray emitter, or a combination thereof.
19. The method of any of paragraphs 1-18, wherein the compound is labeled with a radionuclide selected from the group consisting of $^{3}H$, $^{11}C$, $^{13}C$, $^{14}C$, $^{13}N$, $^{15}O$, $^{17}O$, $^{18}F$, $^{19}F$, $^{75}Br$, $^{76}Br$, $^{77}Br$, $^{82}Br$, $^{82}Rb$, $^{99m}Tc$, $^{123}I$, $^{124}I$, $^{125}I$, $^{131}I$, and any combinations thereof.
20. The method of any of paragraphs 1-20, further comprising allowing to pass a sufficient period of time after said administration of the contrast agent for achieving binding between the contrast agent and the α-synuclein aggregate.
21. The method of any of paragraphs 1-20, wherein the compound is a near infrared (NIR) fluorophore.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Staining of Synuclein Pathology in Human DLB and PD Cases

PD/DLB tissue was stained using standard immunohistochemical techniques using the H3C antibody to synuclein and Alexa488 labeled fluorescent secondary antibody. The sections were imaged with Olympus Microscope using a GFP filter or with a white light broad filter to see synuclein and intracellular lipofuscin auto-fluorescence. As shown in FIG. 1, Lewy bodies and Lewy neuritis, hallmarks of PD and DLB diseases, can be easily detected.

Post-mortem midbrain tissue from DLB and PD patients was obtained from the HBTRC Brain Bank at McLean Hospital. Tissue was fixed with formalin and immuno-stained with H3C primary antibody for synuclein and Alexa488 or Cy5 (not shown) conjugated secondary antibody. Immuno-stained tissue was incubated with fluorescent dyes in PBS at concentrations of 500 nM, 2 µM, and 5 µM for 30 minutes. Slides of tissue were imaged with Olympus Microscope at 60× with appropriate filter set.

Figure 2A:
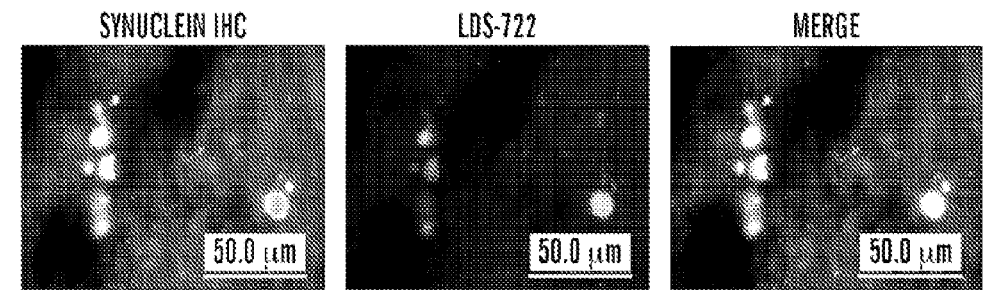
FIGS. 2A-2C are microscope images showing contrast agents had various staining patterns on Lewy body (LB) and Lewy neurites (LN) in DLB post-mortem midbrain tissue.
Figure 2B:
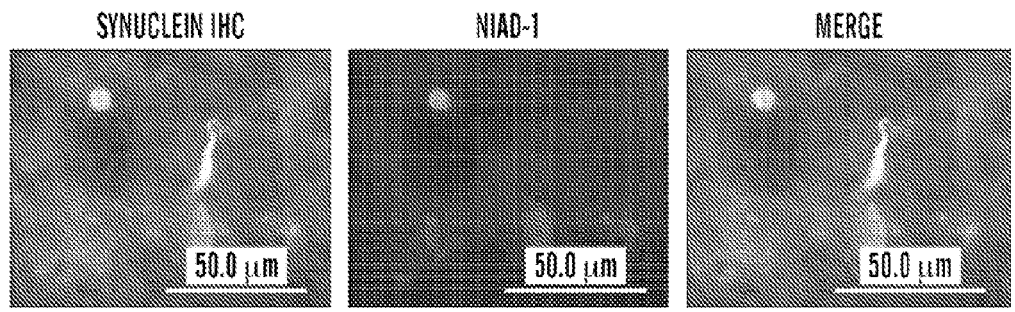
Figure 2C:
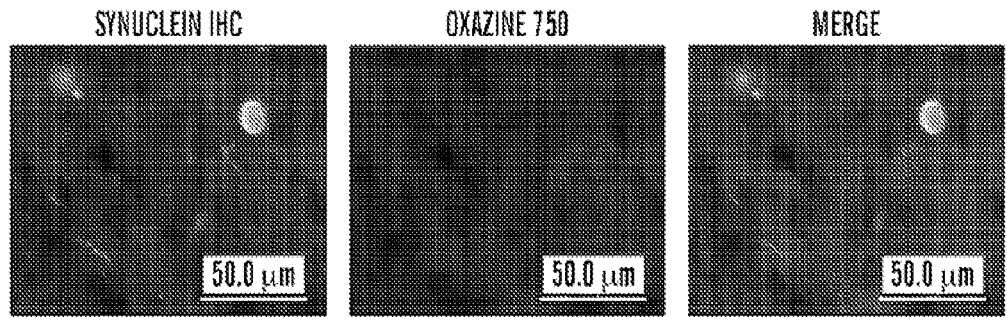

Examples of common staining patterns are illustrated in FIG. 2. As seen in FIG. 2 contrast agents showed variable binding affinities to Lewy bodies and neurites. Most contrast agents did not bind Lewy neurites. Many contrast agents were specific to Lewy bodies but had lower contrast and a few had higher contrast.

Example 2

Tested Agents Show Variable Staining of Plaques and NFT

Figure 3A:
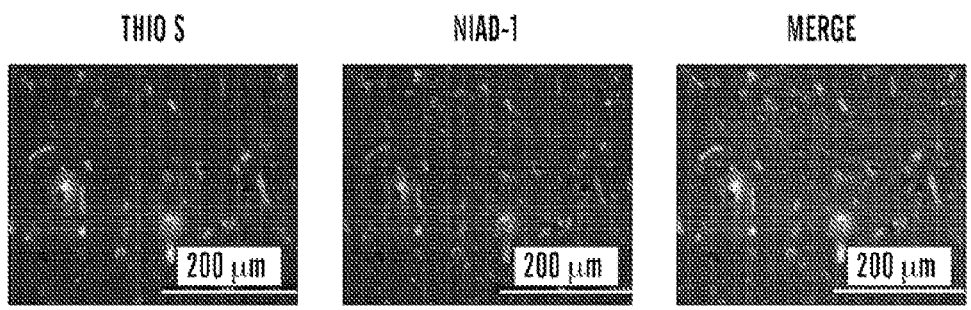
FIGS. 3A and 3B are is microscope images showing some of the tested compounds are specific to Lewy pathology and do not bind plaques or neurofibrillary tangles in AD sections.
Figure 3B:
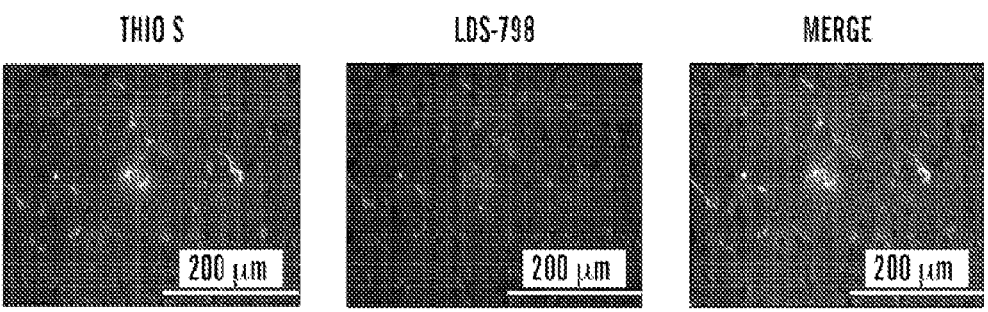

Paraffin-embedded formalin-fixed tissue from the temporal lobe of AD patients was obtained through the MA ADRC Brain Bank. Sections were stained with 0.05% Thio S to visualize plaques and NFT. Tissue was then stained with 5 µM dye in PBS. Slides were imaged on an Olympus Microscope at 20×, with a GFP emission filter for Thio S, and appropriate emission ranges for the dyes. Representative images are shown below. Many dyes had positive (+) staining for both plaques and tangles; however, some did not bind (−) AD pathology, suggesting a specificity for synuclein PD pathology. As seen in FIG. 3, some contrast agents were specific to Lewy body pathology and do not bind plaques or neurofibrillary tangle in AD sections.

Example 3

Contrast Agents can Cross the Blood-Brain Barrier for In Vivo Imaging

Figure 4A:
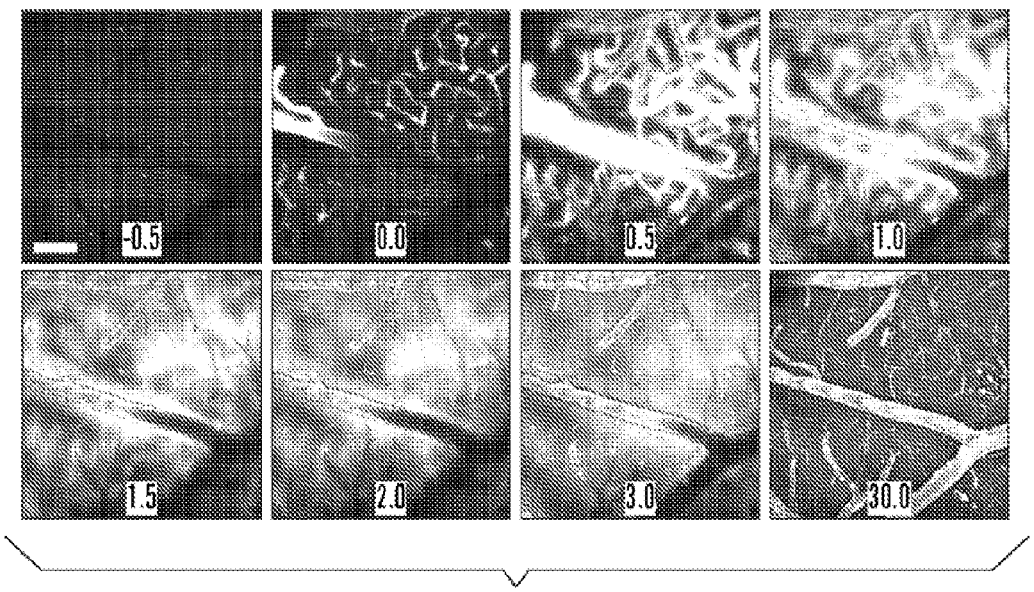
FIGS. 4A and 4B are microscope images showing compounds (can be visualized crossing the blood-brain barrier with in vivo imaging.

Pittsburgh Compound B (PiB), a clinical PET ligand for amyloid imaging, was injected into the tail vein of a PD/APP transgenic mouse (18 mo) at a concentration of 10 mg/kg. The PiB compound was shown to cross the BBB within 1 minute of IV injection. Images were taken with a BIO-RAD MRC1024 multi-photon microscope. A time course of the PiB IV injection is shown in FIG. 4. PiB fluorescence was seen within the vessel, crossing the vessel wall into the parenchyma, then binding amyloid pathology, and clearing the tissue rapidly. See Bacskai B J, et al., PNAS, 2003, 100: 12462-12467p. This shows that compounds can be visualized crossing the blodd-brain barrier with in vivo imaging.

Figure 4B:
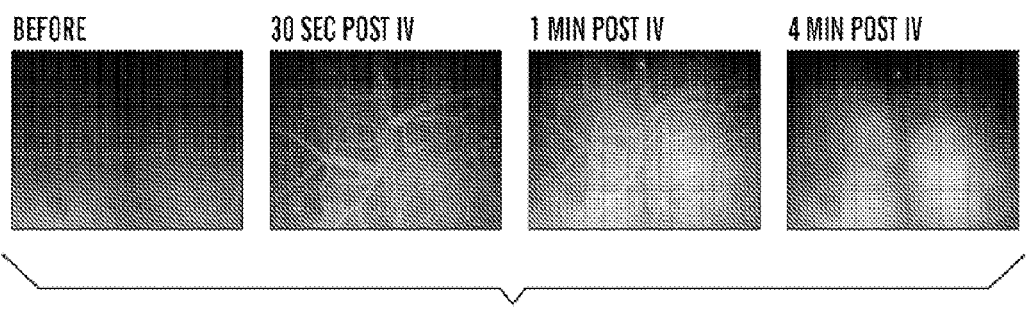

LDS798, which binds Lewy body pathology, was solubilized in 6% DMSO and 1×PBS at a concentration of 10 mg/kg and then injected IV into a wildtype mouse. Wide field fluorescence images were taken with a CCD camera on an Olympus microscope. The time course of fluorescence in the brain and vasculature during the bolus injection are shown in FIG. 4B. This shows directly that LDS798 crosses BBB and rapidly enters brain.

FIG. 5 shows the structures and Table 1 lists properties of some of the compounds used in this study. Table 2 summarizes the results from the work presented herein.

TABLE 1

| Compound | Molecular Weight g/mol | Excitation Peak (nm) | Emission Peak (nm) | Log P |
| --- | --- | --- | --- | --- |
| 3-3'-DTDCI | 572 | 656 | 673 | 2.31 |
| LDS 722 | 379 | 495 | 702 | 1.04 |
| LDS 759 | 515 | 558 | 736 | 2.88 |
| LDS 798 | 429 | 558 | 766 | 1.8 |
| NIAD-1 | 550 | 540 | 720 | 1.52 |
| Nile Red | 318 | 552 | 620 | 3.51 |
| RD-1 | 413 | 600 | 615 | 1.39 |
| THK-265 | 350 | 640 | 663 | TBD |
| LDS 730 | 431 | 603 | 668 | TBD |
| Nile Blue 690 ClO4 | 418 | 624 | 660 | TBD |
| HITC ClO4 | 509 | 751 | 790 | TBD |
| Stilbene 420 | 563 | 353 | 425 | TBD |

TABLE 2

| Compound | Lewy Bodies Contrast | Lewy Neurites Contrast | SynT-Syn1 Cell Model | Venus-YFPSyn Cell Model | Syn-GFP Mice | AD Plaque Contrast | AD NFT Contrast | BBB Crossing |
| --- | --- | --- | --- | --- | --- | --- | --- | --- |
| 3-3'-DTDCI | + | − | + | + | − | + | − | − |
| LDS 722 | ++ | + | − | − | − | ++ | ++ | TBD |
| LDS 759 | + | − | + | + | + | − | − | TBD |
| LDS 798 | ++ | − | − | − | − | − | − | + |
| NIAD-1 | + | − | + | − | − | + | + | + |
| Nile Red | + | − | + | + | + | − | − | + |
| RD-1 | + | − | + | − | − | + | − | + |
| THK-265 | + | − | + | − | − | + | − | − |
| LDS 730 | + | − | N/A | N/A | − | +/− | + | TBD |
| Nile Blue 690 ClO4 | ++ | − | N/A | N/A | + | − | − | TBD |
| HITC ClO4 | + | − | N/A | N/A | − | − | − | TBD |
| Stilbene 420 | ++ | + | N/A | N/A | N/A | ++ | + | TBD |

Discussion

The development of an in vivo imaging approach for Parkinson's disease (PD) patients would revolutionize clinical diagnosis and scientific research. In the same way that imaging with PiB has contributed to Alzheimer's research, inventors discovered a number of compounds that are specific for PD pathology to allow disease progression and drug efficacy to be imaged directly with PET.

The inventors have identified several compounds that bind PD pathology in human midbrain tissue. Many of the tested compounds only bound Lewy bodies. Some bound both Lewy bodies and Lewy neurites. Additionally, some of the tested compounds showed specificity for synuclein pathology and did not bind AD plaques or tangles. Further, several of the compounds were able to cross the blood-brain barrier. Thus, compounds disclosed herein can be used for in vivo imaging agents for diagnosis of α-synuclein aggregation associated disorders such as Parkinson's disease.

In addition, the inventors also discovered that synuclein cell culture models and Syn-GFP mouse model do not predict compound binding to the human pathological hallmarks, Lewy bodies and Lewy neurites.

Thus, using fluorescent approaches to screen compounds, the inventors characterized several compounds that have specificity for PD pathology. Because many of these compounds are able to cross the blood-brain barrier, they can be used as PET imaging ligands for α-synuclein aggregation associated disorders.

All patents and other publications identified in the specification are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for in vivo imaging of an α-synuclein aggregate, the method comprising:
   a) administering, to a subject in need thereof, a detectable amount of a compound selected from the group consisting of 3,3'-diethylthiadicarbocyanine iodide (3-3'-DTDCI); 4-[4-[4-(dimethylamino)phenyl]-1,3-butadienyl]-1-ethyl-pyridinium perchlorate (LDS 722); LDS 759; 4-[4-[4-(dimethylamino)phenyl]-1,3-butadienyl]-1-ethyl quinolinium (LDS 798); 9-diethylamino-5-benzo[α]phenoxazinone (Nile Red); THK-265; 2-[4-[4-(dimethylamino)phenyl]-1,3-butadienyl]-1,3,3-trimethyl-3H-indolium perchlorate (LDS 730); 5-amino-9-(diethylamino)-benzo[a]phenoxazin-7-ium perchlorate (Nile Blue 690 $ClO_4$); 2-[7-(1,3-dihydro-1,3,3-trimethyl-2H-indol-2-ylidene)-1,3,5-heptatrienyl]-1,3,3-trimethyl-3H-indolium perchlorate (HITC $ClO_4$); 2,2"-([1,1'-biphenyl]-4.4'-diyldi-2,1-ethenediyl)bis-benzenesulfonic acid disodium salt (Stilbene 420); analogs, isomers and pharmaceutically acceptable salts thereof; and any combinations thereof; and
   b) detecting the contrast agent bound to the α-synuclein aggregate to image the α-synuclein aggregate.

2. The method of claim 1, wherein the subject is suspected of having a Lewy body or Lewy neurite associated disorder.

3. The method of claim 2, wherein the Lewy body or Lewy neurite associated disorder is Parkinson's disease.

4. The method of claim 1, wherein the α-synuclein aggregate is located in the brain of the subject.

5. The method of claim 1, wherein the detectable amount of the compound is from about 1 μg/kg body weight to about 250 mg/kg body weight.

6. The method of claim 1, wherein said administering is by intravenous injection.

7. The method of claim 1, wherein the subject is human.

8. The method of claim 1, wherein said detecting is by infrared imaging, multiphoton imaging, gamma imaging, magnetic resonance imaging (MRI), magnetic resonance spectroscopy, or a combination thereof.

9. The method of claim 1, wherein said detecting is by near-infrared fluorescence (NIRF) imaging, position emission tomography (PET) imaging, single-photon emission computed tomography (SPECT or SPET) imaging, X-ray fluorescence imaging, PET with concurrent computed tomography (PET/CT), PET with concurrent magnetic CT imaging (SPECT/CT), or a combination thereof.

10. The method of claim 1, wherein the compound is labeled with a radiolabel, fluorescent label, chemiluminescent label, or a combination thereof.

11. The method of claim 1, wherein the compound is labeled with a beta-emitter, gamma-emitter, positron-emitter, x-ray emitter, or a combination thereof.

12. The method of claim 1, wherein the compound is labeled with a radionuclide selected from the group consisting of $^3H$, $^{11}C$, $^{13}C$, $^{14}C$, $^{13}N$, $^{15}O$, $^{17}O$, $^{18}F$, $^{19}F$, $^{75}Br$, $^{76}Br$, $^{77}Br$, $^{82}Br$, $^{82}Rb$, $^{99m}Tc$, $^{123}I$, $^{124}I$, $^{125}I$, $^{131}I$, and any combinations thereof.

13. The method of claim 1, further comprising allowing to pass a sufficient period of time after said administration of the contrast agent for achieving binding between the contrast agent and the α-synuclein aggregate.

14. The method of claim 1, wherein the compound is a near infrared (NIR) fluorophore.

15. A method for detecting, diagnosing, or determining regression, progression, or onset of a Lewy body or Lewy neurite associated disorder, the method comprising:
   a) administering, to a subject in need thereof, a detectable amount of a compound selected from the group consisting of 3-3'-DTDCI, LDS 722, LDS 759, LDS 798, Nile Red, THK-265, LDS 730, Nile Blue 690 $ClO_4$, HITC $ClO_4$, Stilbene 420, and any combinations thereof; and
   b) detecting the compound bound to α-synuclein aggregate to determine the level of binding of the contrast agent, wherein an increase in the level of binding relative to a control level of binding indicates that the subject is suffering from or is at risk of developing an α-synuclein aggregate associated disorder.

16. A method of evaluating a treatment for a Lewy body or Lewy neurite associated disorder, the method comprising:
   a) administering a first detectable amount of a compound to a subject undergoing treatment for a Lewy body or Lewy neurite associated disorder to obtain a first level of binding of the compound to α-synuclein aggregate in the subject;
   b) detecting the compound bound to α-synuclein aggregate to determine the first level of binding of the compound;
   c) administering a second detectable amount of the compound, wherein the second administration is at a time subsequent to the first administration, to obtain a second level of binding of the compound to α-synuclein aggregate in the subject;
   d) detecting the compound bound to α-synuclein aggregate to determine the second level of binding of the compound; and e) comparing the first level of binding with the second level of binding as an indication of the effectiveness of the treatment on the level of α-synuclein aggregate in the subject, wherein the compound is selected from the group consisting of 3-3'-DTDCI, LDS 722, LDS 759, LDS 798, Nile Red, THK-265, LDS 730, Nile Blue 690 $ClO_4$, HITC $ClO_4$, Stilbene 420, and any combinations.

17. A method of detecting α-synuclein aggregates in a tissue, the method comprising:
   a) contacting a compound with a tissue, wherein the contrast agent is selected from the group consisting of 3-3'-DTDC1, LDS 722, LDS 759, LDS 798, Nile Red, THK-265, LDS 730, Nile Blue 690 $ClO_4$ HITC $ClO_4$, Stilbene 420, and any combinations thereof; and
   b) detecting the compound bound to α-synuclein aggregate to determine the level of binding of the compound, wherein the level of biding indicates the amount of α-synuclein aggregate in the tissue.

18. The method of claim 17, wherein the tissue is a brain tissue.

19. The method of claim 17, wherein said contacting is in vitro.

20. The method of claim 17, wherein said contacting is in vivo.

* * * * *